United States Patent [19]

Berninger et al.

[11] Patent Number: 5,856,571
[45] Date of Patent: Jan. 5, 1999

[54] SEMICARBAZIDE-CONTAINING LINKER COMPOUNDS FOR FORMATION OF STABLY-LINKED CONJUGATES AND METHODS RELATED THERETO

[75] Inventors: Ronald W. Berninger, Mukilteo; Mark S. Lodge, Seattle; Stanley Joseph Tarnowski, Jr., Woodinville, all of Wash.

[73] Assignee: CellPro, Incorporated, Bothell, Wash.

[21] Appl. No.: 486,980

[22] Filed: Jun. 7, 1995

[51] Int. Cl.$^6$ .................................................. C07C 281/06
[52] U.S. Cl. .............................. 564/37; 564/18; 564/149; 564/227; 548/304.1
[58] Field of Search ................................ 564/18, 37, 227; 548/304.1

[56] References Cited

U.S. PATENT DOCUMENTS

| | | | |
|---|---|---|---|
| 3,483,207 | 12/1969 | Winkelmann et al. | 564/18 |
| 3,929,530 | 12/1975 | Niles | 149/84 |
| 4,741,900 | 5/1988 | Alvarez et al. | 424/85 |
| 5,137,877 | 8/1992 | Kaneko et al. | 564/18 |

FOREIGN PATENT DOCUMENTS

| | | |
|---|---|---|
| 457 250 A2 | 11/1991 | European Pat. Off. . |
| 605 963 A2 | 7/1994 | European Pat. Off. . |
| WO 93/14779 | 8/1993 | WIPO . |

OTHER PUBLICATIONS

Zimenkovskii et al., Chemical Abstracts, vol. 85, abstract 192481, 1976.
Jacobsen, Chemical Abstracts, vol. 126, abstract 4221, 1996.
Mertelsmann et al., "Purification and in vitro expansion of human peripheral blood progenitor cells recruited by chemotherapy and hematopoietic growth factors," *Database: Cancerlit*, Accession No. 95699455, 1993.
Braslawsky et al., "Adriamycin(hydrazone) — antibody conjugates require internalization and intracellular acid hydrolysis for antitumor activity," *Cancer Immunol. Immunother.* 33: 367–374, 1991.
Braslawsky et al., "Antitumor Activity of Adriamycin (Hydrazone–linked) Immunoconjugates Compared with Free Adriamycin and Specificity of Tumor Cell Killing," *Cancer Research* 50: 6608–6614, 1990.
Green, M., "Avidin," *Adv. Protein Chem.* 29: 85–133, 1975.
Greenfield et al., Evaluation inVitro of Adriamycin Immunoconjugates Synthesized Using an Acid–sensitive Hydrazone Linker, *Cancer Research* 50: 6600–6607, 1990.
Heindel et al., "Hydrazide Pharmaceuticals as Conjugates to Polyaldehyde Dextran: Syntheses, Characterization, and Stability," *Bioconjugate Chem.* 1: 77–82, 1990.
Hurwitz et al., "Soluble Macromolecules as Carriers for Daunorubicin," *Journal of Applied Biochem.* 2: 25–35, 1980.

Kaneko et al., "New Hydrazone Derivatives of Adriamycin and Their Immunoconjugates–a Correlation between Acid Stability and Cytotoxicity," *Bioconjugate Chemistry* 2(3): 133–141, 1991.
King et al., "Preparation of Protein Conjugates via Intermolecular Hydrazone Linkage," *Biochemistry* 25: 5774–5779, 1986.
Kralovec et al., "Synthesis of site–specific methotrexate–IgG conjugates. Comparison of stability and antitumor activity with active–ester–based conjugates," *Cancer Immunol. Immunother.* 29: 293–302, 1989.
Mueller et al., "Antibody Conjugates with Morpholinodoxorubicin and Acid–Cleavable Linkers," *Bioconjugate Chem.* 1(5): 325–330, 1990.
O'Shannessy and Quarles, "Labeling of the oligosaccharide moieities of immunoglobulins," *Journal of Immunological Methods* 99: 153–161, 1987.
O'Shannessy et al., "A Novel Procedure for Labeling Immunoglobulins by conjugation to Oligosaccharide Moieties," *Immunology Letters* 8: 273–277, 1984.
Oshevskii et al., "Incorporation in DNA of Biotinylated Analogues of dUTP and dCTP by DNA Polymerases," *Soviet Journal of Bioorganic Chemistry* 15: 601–609, 1990.
Reeves, R., "Condensations leading to double bonds," in *The Chemistry of the Carbonyl Group*, S. Patai (ed.), Interscience, NY, 1966, pp. 567–619.
Rose et al., "Preparation of Well–Defined Protein Conjugates Using Enzyme–Assisted Reverse Proteolysis," *Bioconjugate Chem* 2: 154–159, 1991.
Trail, et al., Cure of Xenografted Human Carcinomas by BR96–Doxorubicin Immunoconjugates, *Science* 261: 212–215, 1993.
Webb II and Kaneko, "Synthesis of 1–(Aminooxy)–4–[(3–nitro–2–pyridyl)dithio]butane and 1–(Aminooxy)–4–[(3–nitro–2–pyridyl)dithio]but–2–ene, Novel Heterobifunctional Cross–Linking Reagents," *Bioconjugate Chem.* 1:96–99, 1990.
Wilchek and Bayer, "Introduction of Avidin–Biotin Technology," *Methods in Enzymology* 184: 5–13, 1990.
Wilchek and Bayer, "The Avidin–Biotin Complex in Bioanalytical Applications," *Analytical Biochemistry* 171: 1–32, 1988.
Willner et al., "(6–Maleimidocaproyl)hydrazone of Doxorubicin–A New Derivative for the Preparation of Immunoconjugates of Doxorubicin," *Bioconjugate Chem.* 4: 521–527, 1993.

*Primary Examiner*—Richard L. Raymond
*Attorney, Agent, or Firm*—Seed and Berry LLP

[57] ABSTRACT

Linker compounds for formation of stably-linked conjugates are disclosed. Such linker compounds are semicarbazide-containing linker compounds useful in forming conjugates having stable semicarbazone linkages. The stably-linked conjugates have utility in a variety of immunodiagnostic and separation techniques.

14 Claims, 1 Drawing Sheet

Fig. 1

SEMICARBAZIDE-CONTAINING LINKER COMPOUNDS FOR FORMATION OF STABLY-LINKED CONJUGATES AND METHODS RELATED THERETO

TECHNICAL FIELD

The present invention relates generally to linker compounds for the formation of stably-linked conjugates and, more specifically, to stable semicarbazone-linked conjugates and methods relating to their use.

BACKGROUND OF THE INVENTION

Biological molecules are often coupled to other molecules or compounds for use in bioanalytical or biopharmaceutical applications. The covalent combination of a biological molecule and another molecule or compound is generally referred to as a "conjugate." For example, the term "immunoconjugate" generally refers to a conjugate composed of an antibody or antibody fragment and some other molecule such as a label compound (e.g., a fluorophore), a binding ligand (e.g., a biotin derivative), or a therapeutic agent (e.g., a therapeutic protein or toxin). These particular conjugates are useful in reporting the presence of the antibody, binding or capturing the antibody, and targeting the delivery of a therapeutic agent to a specific site, respectively.

Conjugates are prepared by covalently coupling one of the conjugate components to the other. For instance, an immunoconjugate may be prepared by coupling a label compound, a binding ligand, or a therapeutic agent to an antibody or antibody fragment. Often the coupling involves the use of a linker compound or molecule which serves to join the conjugate components. For example, a typical immunoconjugate is composed of a biotin component covalently coupled to an antibody component through a linker. Because the linker is typically chosen to provide a stable coupling between the two components, the usefulness of the conjugate is generally limited by the stability of the linkage between the conjugate components—that is, the greater the stability of the linkage between the components of a conjugate, the more useful and effective the conjugate. Depending upon a conjugate's use, a wide variety of conjugates may be prepared by coupling one conjugate component to another via a linker. Virtually an endless number of combinations of a biological molecule coupled to a label compound, binding ligand or therapeutic agent have been joined to create conjugates suitable for a particular purpose or need.

An example of a useful and widely employed class of conjugates include biotin conjugates. Biotin is a naturally occurring vitamin which has an extremely high binding affinity ($K_d \approx 10^{-15} M^{-1}$) for avidin and streptavidin. Because of the affinity of biotin for avidin, biotin-containing conjugates have been widely used in bioanalytical procedures including immunoassays, affinity chromatography, immunocytochemistry, and nucleic acid hybridization (see, e.g., Green, *Adv. Protein Chem.* 29:85, 1975; Wilchek and Bayer, *Anal. Biochem.* 171:1, 1988; Wilchek and Bayer, *Meth. Enzymol.* 184:5, 1990). Bioanalytical assays often take advantage of the high binding affinity of biotin for avidin through the covalent coupling of biotin to one of the assay components. To this end, biotin may be covalently coupled to many different types of molecules, including proteins, such as antibodies, antibody fragments, enzymes and hormones; nucleic acids such as oligonucleotides and a nucleic acid probes; and smaller molecules such as drugs or other similar compounds. Moreover, in some applications biotin may be coupled to a solid phase or support.

The covalent coupling of biotin to another molecule involves bond formation through chemical reaction between suitable chemical functional groups. For the coupling of biotin to a molecule such as an antibody or enzyme, a reactive biotin derivative is generally used. Reactive biotin derivatives for conjugation may readily be prepared from biotin, and are most commonly carboxylic acid derivatives or, in some cases, nucleophilic derivatives such as amine or hydrazide derivatives. Common reactive biotin derivatives include reactive biotin esters such as an N-hydroxysuccinimide (NHS) ester. For example, biotin NHS esters may be conveniently attached to proteins and peptides through a free amino group, such as the epsilon amino group on lysine residues. Other reactive biotin derivatives include nucleophilic derivatives, such as biotin hydrazide, which may be conjugated to glycoproteins through aldehyde groups generated by oxidation of their carbohydrate groups. Reactive biotin derivatives are commercially available from a variety of sources including Sigma (St. Louis, Mo.), Pierce (Rockford, Ill.), and Molecular Probes (Eugene, Oreg.). Many of these biotin derivatives contain various chemical groups between the biotin moiety and the reactive group. Methods of conjugating biotin derivatives to proteins have been described in numerous publications (see, e.g., Harlow and Lane, *Antibodies. A Laboratory Manual*, NY: Cold Spring Harbor Laboratory, 1988, pp. 340–341; O'Shannessy and Quarles, *J. Imnmunol. Methods* 99:153, 1987; O'Shannessy et al., *Immunol. Letters* 8:273, 1984; Rose et al., *Bioconjug Chem.* 2: 154, 1991).

In addition to biotin, other compounds are commonly coupled to biological molecules for use in bioanalytical procedures. Typically, these compounds are useful in labeling the biological molecule for detection purposes. Common labeling compounds include fluorescent dyes, as well as ligands for binding to their respective binding partners. Examples of common fluorescent dyes used for this purpose include fluorescein and rhodamine, and examples of ligands for binding to their binding partners include drug compounds such as digoxigenin and β-lactam antibiotics. Numerous other compounds suitable for use as labels in specific binding techniques have also been described in the literature. Like biotin, these compounds are generally derivatized to contain functional groups that react readily with the biological molecule. For example, fluorescein isothiocyanate is a reactive fluorescein derivative which may readily be conjugated to proteins through their sulfhydryl groups.

Effective conjugation of a compound, such as biotin or a fluorescent dye, to a biological molecule generally requires that the resulting labeled conjugate retain the bioactivity of the biological molecule. A conjugate may have only limited utility if, upon coupling, the functional activity of the biological molecule is diminished or lost. For example, for an antibody conjugate, retention of antigen binding activity (immunoreactivity) is of foremost importance. Because some antibodies lose immunoreactivity upon labeling of their free amino groups, presumably due to the presence of these groups in the antigen binding site of the antibody (see Harlow and Lane), the site or sites at which a label is attached to a biological molecule is of considerable importance. Similarly, some enzymes contain free amino groups in their active sites which, upon their use as a labeling site, may result in a loss of enzymatic activity. Many enzymes also contain sulfhydryl groups in their active sites and are inactivated by labeling with sulfhydryl-reactive compounds such as fluorescein isothiocyanate.

In addition to retaining bioactivity, the stability of the conjugate with respect to linkage of the compound to the biological molecule is very important. For example, loss of a label from a conjugate typically results in the loss of ability to follow the conjugate in a bioanalytical procedure. In an attempt to provide stable linkages, conjugates are often coupled through amide and hydrazone bonds. Amide linkages are formed by reaction between an amino group and a carboxylic acid group, and hydrazone linkages result from reaction of a carbonyl group (such as an aldehyde group) and a hydrazine group. The relatively high stability of these linkages has led to their wide use in conjugation techniques (see, e.g., O'Shannessy et al., 1984; Reeves, in *The Chemistry of the Carbonyl Group*, S. Patai (ed.), NY: Interscience, 1966, pp. 567–619). However, while such conjugates may be stable at neutral pH, these conjugates become unstable at acid pH (Hurwitz et al., *J. Applied Biochem.* 2:23, 1980; Kaneko et al., *Bioconj. Chem.* 2:133, 1991). In fact, investigators have even exploited the pH-dependent stability of the hydrazone bond to design antibody-drug conjugates that retain the drug in the generally neutral pH environment of the peripheral circulation, and release the drug when the conjugate is exposed to an acidic environment such as is found in certain cell organelles.

Because of the perceived stability of hydrazone and amide bonds, the usual solution to the problem of activity loss by a hydrazone- or amide-linked labeled conjugate is to use more of the conjugate (i.e., to re-titer the conjugate) or to prepare a "fresh" conjugate. For example, where loss of functional activity of a biotin-antibody conjugate has been observed, it has been generally assumed that this loss is due to a loss in immunoreactivity of the antibody portion of the conjugate. This assumption, however, may be invalid in many instances. Rather, depending upon storage conditions, the immunoreactivity of the antibody portion of the conjugate may be undiminished, and the effectiveness of the conjugate is compromised by use of a linker that is unstable at the storage and/or use conditions.

Accordingly, there is a need in the art for improved linkages for conjugating a biological molecule with, for example, a label compound, binding ligand or agent, or therapeutic agent. Such linkages should have enhanced stability such that the effectiveness of the conjugate is not diminished through storage and/or use conditions. The present invention fulfills these needs and provides further related advantages.

SUMMARY OF THE INVENTION

In brief, this invention is directed to a linker compound and a stably-linked conjugate, and more specifically to a semicarbazide-containing linker compound useful for forming a stably-linked conjugate. The present invention discloses a stably-linked conjugate having a first component covalently linked to a second component through a stable semicarbazone linkage. The stably-linked conjugate of this invention has utility in a variety of immunodiagnostic and separation techniques.

In one embodiment, this invention discloses a semicarbazide-linker compound having the structure:

$$X-(CH_2)_n-R_1-C(=R_2)-R_3-NH-NH_2$$

where X, n, $R_1$, $R_2$, and $R_3$ are as identified in the following detailed description. The invention also discloses protected semicarbazide-containing linker compounds.

In another embodiment, component-linker compounds are also disclosed. The component-linker compounds of this invention include a semicarbazone-linked component-linker compound having the structure:

$$X-(CH_2)_n-R_1-C(=R_2)-R_3-NH-N=C(R_4)-B$$

where X, n, $R_1$, $R_2$, $R_3$, $R_4$, and B are as identified in the following detailed description; and a covalently linked component-linker compound having the structure:

$$A-Y-(CH_2)_n-R_1-C(=R_2)-R_3-NH-NH_2$$

where A, Y, n, $R_1$, $R_2$, and $R_3$ are as identified in the following detailed description.

As mentioned above, in yet another embodiment of this invention, a stably-linked conjugate is disclosed having the structure:

$$A-Y-(CH_2)_n-R_1-C(=R_2)-R_3-NH-N=C(R_4)-B$$

where A, Y, n, $R_1$, $R_2$, $R_2$, $R_4$ and B are as identified in the following detailed description.

These and other aspects of the invention will be apparent upon reference to the following detailed description. To this end, various references are set forth herein which describe in more detail certain procedures, compounds and/or compositions, and are hereby incorporated by reference in their entirety.

DESCRIPTION OF THE INVENTION

The present invention is generally directed to a linker compound useful for forming a stable linkage between a conjugate of multiple components. In the case of a two component conjugate, the linker moiety forms a stable linkage between a first component and a second component. While the nature of the individual first and second components may be widely variable, this invention discloses linkage compounds that have enhanced stability over other linkers that have been previously used for this purpose. More specifically, this invention is directed to a semicarbazide linker that is capable of forming a stable semicarbazone linkage with a carbonyl-containing component. The semicarbazone linkage facilitates the stable linkage of the first component to the second component, and offers significant advantages over known linkers.

Accordingly, in one embodiment, the present invention discloses stably-linked conjugates comprising a first component covalently linked to a second component through a stable linkage facilitated by a linker compound. Such conjugates may be generally represented by structure I:

$$A\text{-linker-}B \qquad\qquad I$$

where A is a first component and B is a second component, and wherein the linker is covalently joined to both A and B, with the linkage to B being a semicarbazone linkage. As used herein, the term "component" is use to refer to either the first component or the second component, and the term "components" is used to refer to both the A component and the B component. The components of the present invention are described in more detail below.

In one aspect of this invention, linker compounds are disclosed. Such linker compounds join the conjugate components through covalent bond formation. The linker compounds of the present invention have a first reactive group for coupling the A component, and a second semicarbazide reactive group for coupling the B component. Thus, the linker compounds of the present invention may be characterized as semicarbazide-containing linker compounds, and are represented by structure II:

where X is a functional group capable of forming a covalent linkage to the A component of structure I; n=$_{1-12}$; $R_1$ is selected from $CH_2$, NH, O, S and phenyl; $R_2$ is selected from O, NH and S; and $R_3$ is an optional phenyl moiety.

The semicarbazide-containing linker compounds of this invention are capable of reacting with a carbonyl moiety of the B component, such as an aldehyde or ketone moiety, to form a stable semicarbazone linkage with the B component defined herein as "—$R_1$—C(=$R_2$)—$R_3$—NH—N=C($R_4$)—B," where $R_1$, $R_2$ and $R_3$ are as defined above, and $R_4$ is selected from hydrogen and a $C_1$–$C_{12}$ alkyl group, typically a $C_1$–$C_6$ alkyl group. In a preferred embodiment, the semicarbazide moiety of the linker compound is reacted with an aldehyde moiety of the B component, and $R_4$ is hydrogen.

Depending upon the selection of $R_1$, $R_2$ and $R_3$, the present invention provides a variety of semicarbazide-containing linker compounds. Preferred linker compounds include oxo semicarbazide compounds having the structure X—$(CH_2)_n$—NH—C(=O)—NH—$NH_2$; thio semicarbazide compounds having the structure X—$(CH_2)_n$—NH—C(=S)—NH—$NH_2$; imino semicarbazide compounds having the structure X—$(CH_2)_n$—NH—C(=NH)—NH—$NH_2$; and aryl oxo semicarbazide compounds having the structure X—$(CH_2)_n$—NH—C(=O)—$C_6H_4$—NH—$NH_2$, where X and n are as defined above for structure II.

In addition to forming a semicarbazone linkage to the B component of structure I, the linker compounds of the present invention also possess a functional group, "X," capable of covalent coupling to the A component. Thus, the semicarbazide-containing linker compounds of this invention are bifunctional compounds (i.e., the linker compounds have two chemically reactive sites). In the practice of utilizing these bifunctional linker compounds, chemical reaction is ordinarily carried out selectively at one reactive site or the other (i.e., either at X— or —$R_1$—C(=$R_2$)—$R_3$—NH—$NH_2$). In many instances the reactivity of X is compatible with the reactivity of the semicarbazide group, and such selectivity may be directly achieved. For example, when X is a carboxylic acid and the desired chemical reaction involves coupling the semicarbazide group to an aldehyde-containing component, the semicarbazide-containing linker compound having the carboxylic acid group may be directly reacted with the aldehyde-containing compound. However, in some cases, selective reactivity at one reactive site may require the temporary blocking of reaction at the other reactive site. For example, for semicarbazide-containing linker compounds where X is an amino group, the linker compound has two similarly reactive sites (i.e., the amino group, —$NH_2$; and the semicarbazide group, —$R_1$—C(=$R_2$)—$R_3$—NH—$NH_2$). As such, selective reaction of one group in the presence of the other may not be possible. Similarly, when one reactive site is reactive toward the other, the two may react with each other. In such a case, to prevent intramolecular reaction or intermolecular crosslinking, one of the reactive groups may be temporarily blocked. For example, for semicarbazide-containing linker compounds where X is an electrophilic group, such as an NHS ester or an isothiocyanate, the semicarbazide group will couple with such an electrophilic group (either intra- or intermolecularly). In this case, coupling of the X group to form a covalent linkage Y to a component A may be achieved by temporarily blocking the semicarbazide group. Alternatively, if the coupling of the semicarbazide group is desired to form an semicarbazone linkage with a component B, then the X group may be temporarily blocked. The temporary blocking of one reactive site to facilitate selective reaction at the other reactive site may be accomplished through the use of suitable protecting groups.

Thus, in one embodiment of this invention, protected compounds of structure II are disclosed having the structures:

where X, n, $R_1$, $R_2$, and $R_3$ are as defined above, and P and P' are suitable protecting groups.

To appreciate the use of protecting groups in the preparation of the compounds of the present invention, an overview of their synthesis is illustrative. Briefly, semicarbazide-containing linker compound II reacts through its semicarbazide group to form an semicarbazone-linked component-linker compound III (see structure III below). When X is either reactive toward the carbonyl group of component B or reactive toward the semicarbazide group, the X group may be protected. Alternatively, when semicarbazide-containing linker compound II reacts through its X group to form a covalently-linked component-linker compound IV (see structure IV below), the semicarbazide group of II may be protected if it is either reactive toward the reactive group of component A or reactive toward the X group. Accordingly, depending upon the component-linker compound to be formed as well as the functional group to be protected, a suitable protecting group may be selected. Such suitable protecting groups are well known in the art (see, e.g., Greene, T. W., *Protective Groups in Organic Synthesis*, John Wiley & Sons, New York, 1981). For the protection of the semicarbazide group, suitable protecting groups include amino protecting groups such as those described in the above mentioned reference (Chapter 7). Similarly, suitable protecting groups may be used to protect, for example, a hydroxy group (see, e.g., Greene, Chapter 2); a carbonyl group (see, e.g., Greene, Chapter 4); a carboxyl group (see, e.g., Greene, Chapter 5); a thiol group (see, e.g., Greene, Chapter 6); and an amino group (see, e.g., Greene, Chapter 7).

In the event that a protecting group is used to protect either the X group or the semicarbazide group of II, the protecting group may then be removed to provide the semicarbazone-linked and covalently-linked component-linker compounds of structures III and IV, respectively. More specifically, the deprotection of the X group gives component linker III below which may then be covalently coupled to component A to provide a stably-linked conjugate (see structure VII below), and the deprotection of the semicarbazide group yields component linker IV below which may be linked to component B through an semicarbazone linkage to produce a stably-linked conjugate of this invention.

With regard to functional group X, suitable functional groups include carboxylic acid groups, amine groups, hydrazide groups, oxime groups, alcohol groups, thiol groups, isocyanate groups, thioisocyanate groups, maleimide groups, reactive halogen groups, and reactive carboxylic acid groups. Suitable reactive halogen groups include α-halocarbonyl compounds, and reactive carboxylic acid groups include acid halides, reactive esters, and anhydrides. In a preferred embodiment, X of structure II is selected from —COOH, —NH$_2$, —CONH$_2$, —OH, —SH and —CN In a further embodiment, the covalent linkage between the A component and the linker compound may be a semicarbazone linkage, in which case the X group may be a semicarbazide or a carbonyl moiety (such as an aldehyde or ketone moiety). It is appreciated that in some instances functional group X may be protected as described above.

In another aspect of the present invention, component-linker compounds are disclosed. As used herein, a "component-linker compound" comprises a component covalently linked to a linker compound. The component-linker compounds of this invention include both covalently-linked component-linker compounds and semicarbazone-linked component-linker compounds.

A semicarbazone-linked component-linker compound comprises a component joined to a linker compound through a semicarbazone linkage, and is represented by structure III:

X—(CH$_2$)n—R$_1$—C(=R$_2$)—R$_3$—NH—N=C(R$_4$)—B    III where X, n, RI, R$_2$, R$_3$, R$_4$ and B are as defined above.

Similarly, a covalently-linked component-linker compound comprises a component joined to a linker compound through a covalent linkage, and is represented by structure IV:

A—Y—(CH$_2$)$_n$—R$_1$—C(=R$_2$)—R$_3$—NH—NH$_2$    IV where A, n, R$_1$, R$_2$, R$_3$, and R$_4$ are as defined above, and Y represents a covalent linkage between the A component and the X moiety of structure II.

The component-linker compound of structures III may be prepared by coupling a carbonyl moiety of the B component to a linker compound through a semicarbazone linkage. For a semicarbazone linkage, coupling typically involves reaction between a carbonyl moiety of the B component and the semicarbazide group of the A component. Preferred carbonyl moieties of the B component include aldehydes and ketones, with aldehydes being most preferred.

Similarly, the component-linker compound of structure IV can be prepared by coupling a reactive moiety of the A component to a linker compound through a covalent linkage, Y. In the case of covalent linkage, such a coupling typically involves reaction between a suitably reactive moiety of the A component and a complementary reactive X moiety of the linker compound. In this context, suitable covalent linkages include amide linkages, amine linkages, ether linkages, thioether linkages, ester linkages, thioester linkages, urea linkages, thiourea linkages, carbamate linkages, thiocarbamate linkages, Schiff base linkages, reduced Schiff base linkages, oxime linkages, semicarbazone linkages, hydrazone linkages and carbon-carbon linkages. In a preferred embodiment, the covalent linkage is an amide linkage.

Alternatively, the component-linker compounds of this invention may prepared by sequential chemical elaboration, starting from a suitably reactive starting compound, using known organic synthesis techniques.

Representative covalently-linked component-linker compounds of this invention include compounds of the following structures V and VI. In these representative structures, the A component is a biotin derivative covalently joined to the linker compound via an amide bond, and the linker compound contains either an oxo or thio semicarbizide moiety. Such compounds may be prepared from a reactive biotin derivative, such as N—(5-aminopentyl)biotinamide (Molecular Probes, Inc., Eugene, Oreg.). Carbonylation of the 5-amino group with phosgene (or a suitable equivalent, such as carbonyl diimidazole) provides the corresponding isocyanate. Treatment of the isocyanate with hydrazine gives the semicarbazide, as represented by the covalently-linked component-linker compound of structure V:

V

A further representative covalently-linked component-linker compound of this invention may be prepared by repeating the above synthetic procedure for structure V, but substituting thiophosgene (or its equivalent) for phosgene. The product of this reaction sequence is a covalently-linked component-linker compound of structure VI:

VI

While the synthesis of representative component-linker compounds are presented above for purpose of illustration, it should be understood that both the covalently-linked and semicarbazone-linked component-linker compounds of this invention may be readily synthesized by one of ordinarily skill in the field of organic synthesis.

In another aspect, the present invention discloses stably-linked conjugates of structure I above More specifically, the stably-linked conjugates of this invention have structure VII:

A—Y—(CH$_2$)$_n$—R$_1$—C(=R$_2$)—R$_3$—NH—N=C(R$_4$)—B    VII where A, Y, n, R$_1$, R$_2$, R$_2$, R4 and B are as identified above. Such stably-linked conjugates may be prepared by covalently coupling a covalently-linked component-linker compound of structure IV with a further component through a semicarbazone linkage. Alternatively, stably-linked conjugates may be prepared by coupling a semicarbazone-linked component-linker compound of structure III with a further component through a covalent linkage. In either case, the stably-linked conjugates of the present invention comprise a first component covalently linked to a second component through at least one semicarbazone linkage.

The first and second components of the stably-linked conjugates of this invention (designated A and B, respectively, in structure VII) may the same or different, and are distinguished in their mode of attachment to the linker compound. In the case of the A component, it may be attached to the linker compound by any one of numerous covalent linkages. Thus, the A component must have a suitably reactive functional group which can react with functional group X of the linker compound of structure II to yield a covalent bond (designated as Y in structure VII). In contrast, the B component must have a suitably reactive carbonyl moiety (such as an aldehyde or ketone) which can react with the semicarbazide of the linker compound of structure II to yield a semicarbizone linkage.

Generally, the first or A component of the present invention may be a molecule or compound for use in bioanalytical or biopharmaceutical applications, or a solid support. Examples of such molecules and compounds include (but are not limited to) label compounds, binding agents and therapeutic agents. Examples of solid supports include solid particles and other solid surfaces. As mentioned above, the A component must have, or be modified to have, a functional group that allows for its coupling by a covalent linkage with corresponding functional group X of the linker compound. Thus, in the practice of this invention, the A component possesses such a reactive functional group.

As used herein, the term "label compound" refers to any compound that may be used to report, signal or detect, either directly or indirectly, the presence of the linker compound or stably-linked conjugate to which the label is attached. Similarly, a "binding agent" is a molecule or compound which may be used to report, signal or detect through a binding interaction the presence of the linker compound or stably-linked conjugate to which the binding agent is attached. In the practice of the present invention, a label compound includes a carrier molecule such as a protein or polypeptide that bears multiple label compounds. For example, a polylysine multiply labeled with fluorescein is a label compound within the context of this invention. Similarly, a carrier molecule that bears multiple binding agents is included as a binding agent within the context of this invention. Thus, for example, polylysine multiply labeled with biotin is a binding agent. "Therapeutic agents" include, for example, therapeutic proteins and toxins. Examples of suitable therapeutic proteins include (but are not limited to) immunomodulatory cofactors, lymphokines, and cytokines, while representative toxins include (but are not limited to) ricin, abrin diphtheria toxin, cholera toxin, gelonin, pokeweed antiviral protein, tritin, Shigella toxin and Pseudomonas exotoxin A. Numerous label compounds, binding agents and therapeutic agents are known in the art, and may be utilized in the practice of the present invention.

In one embodiment of this invention, the A component may be a binding agent that is capable of binding to a specific binding partner (collectively referred to herein as a "binding pair"). A wide variety of high affinity binding pairs may also be utilized, for example, by preparing and selecting antibodies and antibody fragments which recognize a selected antigen, and by further screening of such antibodies in order to select those with a high affinity (see generally, U.S. Pat. Nos. RE 32,011, 4,902,614, 4,543,439 and 4,411,993; see also *Monoclonal Antibodies, Hybridomas: A New Dimension in Biological Analyses*, Plenum Press, Kennett, McKearn, and Bechtol (eds.), 1980; *Antibodies. A Laboratory Manual*, Harlow and Lane (eds.), Cold Spring Harbor Laboratory Press, 1988). Alternatively, antibodies or antibody fragments may also be produced and selected utilizing recombinant techniques (see William D. Huse et al., *Science* 246:1275–1281, 1989; see also L. Sastry et al., *Proc. Natl. Acad. Sci. USA* 86.5728–5732, 1989; Michelle Alting-Mees et al, *Strategies in Molecular Biology* 3:1-9, 1990)(these references describe a commercial system available from Stratacyte, La Jolla, Calif., which enables the production of antibodies through recombinant techniques).

Examples of high affinity binding pairs other than antibodies include riboflavin/riboflavin binding protein; cytostatin/papain having an affinity of $10^{-14}$M (Bjork and Ylinenjarvi, *Biochemistry* 29:1770–1776, 1990); val-phosponate/carboxypeptidase A having an affinity of $10^{-14}$M (Kaplan and Bartlett, *Biochemistry* 30:8165–8170, 1991); 4CABP/RuBisCo having an affinity of $10^{-13}$M, (Schloss, *J. Biol. Chem.* 263:4145–4150, 1988); tobacco hornworm diuretic hormone/tobacco hornworm diuretic hormone receptor having an affinity of $10^{-11}$M (Reagan et al., *Arch. Insect Biochem. Physiol.* 23:135–145, 1993); and biotin/avidin having an affinity of $10^{-}$M (Richards, *Meth. Enz.* 184:3–5, 1990; Green, *Adv. in Protein Chem.* 29:85, 1985).

In a preferred embodiment of this invention, the A component is biotin, which is readily detectable by virtue of its binding to avidin or streptavidin. For immunoassay and immunocytochemistry applications, avidin or streptavidin may themselves be labeled, either directly or indirectly, or may be bound to a solid support. Examples of immunoassays employing biotin-labeled (biotinylated) ligands and avidin or streptavidin are given in the following references: U.S. Pat. Nos. 4,863,876; 5,028,524; 5,371,516; Hashida et al., *J. Biochem.* 110:486, 1991; Wong et al., *J. Virol Methods* 34:13, 1991; Jaouhari et al., *Clin. Chem* 38:1968, 1992; Oh et al., *Clin. Chem. Acta* 218:59, 1993; Ternynck and Avrameas, *Meth. Enzymol.* 184:469, 1990; Shamsuddin and Harris, *Arch. Pathol. Lab. Med* 107:514, 1983; and Wilchek and Bayer, *Immunol. Today* 5:39, 1984. Nucleic acid hybridization assays can also be performed using a biotinylated probe to visualize a specific sequence of interest. Hybridization assays employing biotinylated probes and avidin or streptavidin are given in the following references: Yamane et al., *Nuc. Acids Symp. Ser.* 21:9, 1989; Gregerson et al., *Clin. Chem. Acta* 182:151, 1989; Szakacs and Livingston, *Ann. Clin. Lab. Sci.* 24:324, 1994; Baretton et al., *Cancer Res.* 54:4472, 1994. Immunoaffinity chromatography employing biotinylated antibodies and immobilized avidin is described in the following references: Hofman et al., *J. Am. Chem. Soc.* 100:3585, 1978, Kasher et al., *Mol. Cell Biol.* 6:3117, 1986; Marie et al., *Biochemistry* 29:8943, 1990; Ruby et al., *Meth. Enzymol.* 181:97, 1990; Bayer et al., *Meth. Enzymol.* 62:308, 1979; U.S. Pat. Nos. 5,225,353; 5,215,927; and 5,262,334.

In addition to binding agents, the A component may be a label compound that reports the presence of the linker compound or stably-linked conjugate to which the label is attached. Examples of suitable labels include optical labels such as fluorescent molecules, enzymes, enzyme substrates, and radionuclides. Suitable optical labels may be detected spectroscopically and include fluorescent, phosphorescent, luminescent, and chromagenic molecules. Among these labels, fluorescent labels are perhaps the most common and well known and include, for example, fluorescein, rhodamine, Texas Red®, and cyanine derivatives as well as fluorescent proteins such as phycobiliproteins. As label compounds, enzymes and enzyme substrates generate detectable signals upon enzymatic action. The use of enzymes as labels is well known. Common enzymes for labeling purposes include, for example, alkaline phosphatase, horseradish peroxidase, β-galactosidase, and luciferase. Typical enzyme substrate labels include chemiluminescent compounds such as dioxetanes which emit light upon enzymatic action. Radioactive labels include compounds that bear radioactive isotopes, for example, radioisotopes of hydrogen, carbon, sulfur, phosphorous, as well as radioactive metals such as Cu-64, Ga-67, Ga-68, Zr-89, Ru-97, Tc-99m, Rh-105, Pd-109, In-111, I-123, I-125,I-131, Re-186, Re-188, Au-198, Au-199, Pb-203, At-211, Pb-212 and Bi-212.

Component A may also be a solid support. In the practice of this invention solid supports include solid particles and other solid surfaces. Solid particles include microparticles and microspheres such as uniform latex particles. Such latex particles may range in size ranging from about 0.010 μm to about 20 μm, and made from a variety of polymers including polystyrene, styrene divinylbenzene, styrene butadiene, styrene vinyltoluene, polyvinyl toluene, polymethylmethacrylate. The particles may be surface modified to include functional groups such as carboxylate, amine, amide, aldehyde, and hydroxyl groups. In addition, the particles may be magnetic for use in separation techniques, or dyed for use in various assays. Solid surfaces include any solid surface used in an analytical technique which utilizes the immobilization of a component, as defined by this invention. Such solid surfaces include, for example, the interior surface of a tube or well such as a test tube or microtiter plate well, the interior surface of a separation or affinity column, and the surface of a membrane such as a cellulose, nitrocellulose, or other synthetic membrane used in bioanalytical techniques.

When A component is a solid support, the present invention provides a stably-linked conjugate in which component B is immobilized to the solid support through an semicarbazone linkage. Such a stably-linked conjugate may be prepared in a stepwise procedure. In a representative procedure, reaction of the amino group of a suitable semicarbazide-containing linker compound of structure IIb with activated carboxylate groups on the surface of the solid support by methods known in the art (see, e.g., Bangs, L. B., Uniform Latex Particles, Seragen Diagnostics Inc., Indianapolis, Ind., 1987) results in covalently linkage of the semicarbazide-containing linker compound to the solid support. Once coupled to the solid support, the protecting groups P' may be removed to yield a solid support having a semicarbazide-modified surface. The semicarbazide-modified solid support is represented by structure IV where A is the solid support (e.g., a latex particle) and Y is an amide linkage. The semicarbazide-modified solid support may then be reacted with a suitable B component to provide a semicarbazone-linked product represented by structure VII.

Alternatively, in a similar manner, semicarbazide-containing linker compounds having structure II where X is a carboxylic acid group may be reacted directly with solid supports having aldehyde-modified surfaces to give semicarbazone-linked surface modified solid phases in which the surface is modified with carboxylic acid groups. Such a carboxylic acid-modified solid support is represented by structure III where X is a carboxylic acid, $R_4$ is hydrogen, and B is the solid support. Coupling of these carboxylic acid groups to, for example, the amino groups of proteins or other amino-containing biological molecules provides a semicarbazone-linked product represented by structure VII where A is a protein or other biological molecule, Y is an amide linkage, $R_4$ is hydrogen, and B is the solid support.

As mentioned above, the A component possesses a functional group to effect covalent coupling to the linker compound. For example, where the A component is biotin, biotin may be directly coupled to the linker compound through biotin's carboxylic acid group. In such a coupling, the covalent linkage between biotin and the linker compound may be accomplished by amide bond formation (e.g., where X of structure II is amine). Alternatively, the A component may contain additional functional groups. For example, where the first component is biotin, commercially available reactive derivatives of biotin contain groups which effectively increase the distance between the biotin moiety and the reactive terminus of the biotin derivative. These biotin derivatives extend the biotin reactive coupling site by the addition of, for example, diamine or amino acid moieties to biotin's carboxylic acid group. Like biotin, the biotin amino acid derivative presents a carboxylic acid functional group for coupling to the linker compound. In contrast, the biotin diamine derivative presents an amino group for coupling to the linker compound, and thus the X moiety of structure II may be a carboxylic acid group. In either case, the covalent linkage between biotin and the linker compound may be accomplished by amide bond formation.

In the practice of the present invention, any stable covalent linkage may be employed to join the A component with the linker compound. For example, when the A component is a label compound such as fluorescein, the label may contain functional groups such as isothiocyanate (i.e., —N=C=S), or a reactive ester such as an N-hydroxysuccinimide ester (i.e., —C(=O)—ONHS), to accomplish covalent linkage of the A component to the linker compound. Both of these fluorescein derivatives are commercially available from a variety of sources, and covalent linkage to the linker compound may be accomplished through thiourea or amide bond formation, respectively.

As mentioned above, the linker compounds of the present invention serve to facilitate the stable linkage of a first component (the A component) to a second component (the B component) to provide a stably-linked conjugate. In the practice of the present invention, the B component may be any molecule or compound identified above with regard to the A component, and which contains (or is modified to contain) a suitably reactive carbonyl moiety, such as an aldehyde or ketone. As with the A component, numerous molecules and compounds are known and may be utilized in this regard.

Typically, the B component is a binding agent or a solid support. For the B component, binding agents generally include proteins and nucleic acids. Suitable proteins include antibodies and antibody fragments. Antibodies may be monoclonal or polyclonal, with monoclonal being preferred. Monoclonal antibodies are usually murine, although ratine and human monoclonals may also be employed. Methods for the production of monoclonal antibodies are well known in the art and are described, for example, in the following references: *Current Topics in Microbiology and Immunology*, vol. 81 (Melchers, F. et al., eds.), NY: Springer Verlag, 1978; *Monoclonal Antibodies* (Kennett et al., eds.), Plenum Press, New York, 1980; *Monoclonal Antibodies in Clinical Medicine* (McMichael and Fabre, eds.), Academic Press, London, 1982. Also known are methods for making chimeric (mouse-human or rat-human) monoclonal antibodies, humanized monoclonal antibodies, and single chain monoclonal antibodies (Choy et al., *Eur. J. Immunol.*

23:2676, 1993; Couto et al., *Hybridoma* 12:485, 1993; Major et al., *Hum. Antibodies Hybridomas* 5:9, 1994; Adair et al., *Hum. Antibodies Hybridomas* 5:41, 1994; Peakman et al., *Hum. Antibodies Hybridomas* 5:65, 1994; Major et al., op. cit.; Poul et al., *Mol Immunol.* 32:101, 1995; Friend et al., *Transplant. Proc.* 27:869, 1995; Olsson et al., *Methods in Enzymology* 92:3, 1983; Buck et al., in *Monoclonal Antibodies and Functional Cell Lines. Progress and Applications* (Kennett et al., eds.), Plenum Press, NY, 1984, p. 275; Dubel et al., *J. Immunol. Methods* 178:201, 1995; Graus-Porta et al., *Mol. Cell Biol.* 15:1182, 1995; and Casey et al., *J. Immunol. Methods* 179:105, 1995; Boulianne et al., *Nature* 312:643, 1984; Shin and Morrison, *Meth. Enzymol.* 178:459, 1989).

Common B components also include receptor molecules, such as lymphokine and hormone receptors, as well as nucleic acid probe molecules, such as DNA, RNA, chimeras and nucleic acid analogs (e.g., PNA). Such probes can be cloned from genomic DNA or from cDNA or can be synthesized by polymerase chain reaction (PCR). Short oligonucleotide probes can be synthesized chemically using commercially available DNA synthesizers.

The stably-linked conjugates of formula VII above may be prepared by coupling a semicarbazone-linked component-linker compound of structure III to an A component having a suitably reactive group to yield a covalent linkage. Alternatively, such conjugates may be made by coupling a covalently-linked component-linker compound of structure IV to a B component having a suitably reactive carbonyl moiety to yield a semicarbazone linkage. The stably-linked conjugates of the present invention are more stable and therefore offer advantages over other similar conjugates in which the components are coupled using existing linkages, such as the commonly used hydrazone linkage.

For use in immunoassays or immunoaffinity chromatography, antibodies are often conjugated to a binding agent, such as biotin, by a linker compound. Such conjugation may be achieved by generation of an aldehyde group on the antibody by mild chemical ($NaIO_4$) or enzymatic (galactose oxidase with or without pretreatment with neuraminidase) oxidation of the antibody's carbohydrate moieties. The aldehyde group is then reacted with a commercially available reagent, such as biotin-X-hydrazide (Molecular Probes, Inc., Eugene, Oreg.) having the structure biotin-$NH(CH_2)_5C(=O)NHNH_2$, yielding a biotin-antibody conjugate. This method has been used with a variety of glycosylated proteins (glycoproteins), including many enzymes, hormones, cytokines and cell membrane proteins.

Reaction of a hydrazide group (i.e., $—CH_2C(=O)NHNH_2$) to an aldehyde group (i.e., —CHO) results in formation of a hydrazone bond (i.e., $—CH_2C(=O)NHN=CH—$). When used to link biotin and an antibody, the hydrazone bond is only moderately stable under normal storage conditions for such conjugates. For example, an biotin-antibody conjugate is typically stored at approximately neutral pH in liquid solution at a temperature between about 0° C. and 4° C. Various preservatives may be added, such as sodium azide or sodium benzoate, to prevent microbial growth. Various stabilizers may also be added, including sugars and sugar alcohols, such as sucrose or glycerol. The hydrazone bond, however, is not stable at all storage and/or use conditions. For example, a biotin-antibody conjugate linked via a hydrazone bond loses biotin over time, as determined by a gradual decrease in the biotin:protein (B:P) ratio. This loss of biotin from the conjugate leads to a loss in the ability to follow the antibody in its intended binding reaction, such as an immunoassay or immunoaffinity chromatography process. In contrast, the semicarbazone-linked conjugates of the present invention are more stable than the corresponding hydrazone-linked conjugates over a greater variety of storage and use conditions.

Example 2 discloses the conjugation of the biotin semicarbazide of structure V above to a mouse monoclonal antibody, and Example 3 illustrates the effect of storage at different pH conditions on the rate of biotin loss compared to a corresponding hydrazone-linked conjugate. Under all conditions tested, the stably-linked conjugate of this invention was more stable than the corresponding hydrazone-linked conjugate. Similarly, Example 4 illustrates the long-term stability of the stable-linked conjugate of Example 2 compared to the corresponding hydrazone-linked conjugate. The results of this experiment show that a stably-linked conjugate of the present invention was significantly more stable than the corresponding hydrazone-linked conjugate.

As noted above, the stably-linked conjugates of this invention are useful, for example, for a variety of immuno-diagnostic and separation techniques. There are a variety of immunoassay formats known to those of ordinary skill in the art for using a conjugate as described herein to detect diagnostic molecules (e.g., antigens that indicate the presence of a disease or infection) in a sample (see, e.g., Harlow and Lane, *Antibodies: A Laboratory Manual*, Cold Spring Harbor Laboratory, 1988). In one such format, the A component may be a binding agent capable of binding to a specific binding partner and the B component may be an antibody that recognizes the molecule of interest. The assay may then be performed by incubating the stably-linked conjugate with the sample, for a period of time sufficient to permit binding of the antibody to the antigen, and then separating the conjugate-antigen complex from the remainder of the sample. Such separation may be achieved by, for example, contacting the sample with an immobilized compound capable of binding to the conjugate-antigen complex. For example, if the A component is biotin, a solid support containing immobilized avidin or streptavidin may be used to remove conjugate-antigen complex from the sample. Bound complex may then be detected using a second binding partner (e.g., Protein A or an antibody that binds to the conjugate-antigen complex.

The solid support may be any solid material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride.

In another format, the immunoassay is a two-antibody sandwich assay. This assay may be performed by first contacting an antibody that has been immobilized on a solid support, commonly the well of a microtiter plate or a membrane, with the sample, such that antigen within the sample is allowed to bind to the immobilized antibody. Unbound sample is then removed from the immobilized antigen-antibody complexes and a stably-linked conjugate is added, wherein the A component is a label compound (e.g., an enzyme (such as horseradish peroxidase), substrate, cofactor, inhibitor, dye, radionuclide, luminescent group, or fluorescent group) and the B component is a second antibody capable of binding to a different site on the antigen. The amount of stably-linked conjugate that remains bound to the solid support is then determined using a method appropriate for the specific label compound.

More specifically, once the antibody is immobilized on the support as described above, the remaining protein binding sites on the support are typically blocked with a suitable blocking agent. The immobilized antibody is then incubated with the sample, and antigen within the sample is allowed to bind to the antibody. Preferably, the incubation time is sufficient to achieve a level of binding that is at least 95% of that achieved at equilibrium between bound and unbound antigen. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, and the stably-linked conjugate may be added to the solid support. The stably-linked conjugate is then incubated with the immobilized antibody-antigen complex for an amount of time sufficient to detect the bound antigen. An appropriate amount of time may generally be determined by assaying the level of binding that occurs over a period of time. Unbound stably-linked conjugate is then removed and bound stably-linked conjugate is detected using the label compound. The method employed for detecting the label compound depends upon the nature of the label compound. For radioactive groups, scintillation counting or autoradiographic methods are generally appropriate. Spectroscopic methods may be used to detect dyes, luminescent groups and fluorescent groups. Enzyme label compounds may generally be detected by the addition of substrate (generally for a specific period of time), followed by spectroscopic or other analysis of the reaction products.

Stably-linked conjugates may also be used for the separation of a specific cell type from a biological sample. For example, a stably-linked conjugate may be employed in which the A component is a binding agent, such as biotin, and the B component is an antibody or other molecule specific for a cell surface antigen of the desired cell type. Such a stably-linked conjugate may be incubated with an appropriate biological sample and allowed to bind to the surface antigen. The cell-conjugate complex may then separated from the remainder of the sample by, for example, contacting the sample with an immobilized compound capable of binding to the cell- conjugate complex. For example, if the A component is biotin, a solid support containing immobilized avidin or streptavidin may be used to remove cell-conjugate complex from the sample. Unbound sample constituents may then be removed by an appropriate wash, and the cell separated from the solid support. Representative cell separation procedures and equipment therefor may be found in, for example, U.S. Pat. Nos. 5,215,927; 5,225,353; 5,240,856 and 5,262,334, and published PCT applications WO 91/16116; WO 92/07243 and WO 92/08988. The use of a stably-linked conjugate for cell selection is presented in Example 5.

In addition to the in vitro uses mentioned above, the stably-linked conjugates of the present invention also have utility for in vivo diagnostic and therapeutic applications. For example, a typical in vivo use would include in vivo imaging, as well as targeted delivery of therapeutic agents.

The following examples are provided for purposes of illustration, not limitation.

EXAMPLES
EXAMPLE 1
SYNTHESIS OF A REPRESENTATIVE COVALENTLY-LINKED COMPONENT-LINKER COMPOUND

A representative covalently-linked component linker, biotin cadaverine semicarbazide, structure V below, was prepared using conventional synthesis techniques. Such compounds are readily obtainable from a variety of companies providing contract organic synthesis services, including, for example, Molecular Probes, Inc., Eugene, Oreg.

V

EXAMPLE 2
SYNTHESIS OF A REPRESENTATIVE STABLY-LINKED CONJUGATE

This example illustrates the synthesis of a representative stably-linked conjugate of this invention by coupling the covalently-linked component-linker of Example 1 to an antibody. (This example also discloses the synthesis of a corresponding conjugate coupled via a hydrazone linkage, which is used for comparison purposes in Examples 3, 4 and 5 below.)

The covalently-linked component-linker compound of structure V (see Example 1) and a commercially available biotin hydrazide, biotin-$NH(CH_2)_5C(=O)NHNH_2$ (Molecular Probes, Inc., Eugene, Oreg.) were conjugated to a mouse monoclonal antibody ($\mu$ $\kappa$) designated 12.8 (Andrews et al., *Blood* 67:842, 1987) according to the method of O'Shannessy and Quarles (*J. Immunol. Methods* 99:153, 1987). Antibody was purified from tissue culture supernatant using standard purification techniques and adjusted to a concentration of 1 mg/mL in 100 mM sodium acetate/300 mM NaCl, pH 5.5.

To a 1 mg/mL antibody solution was added $NaIO_4$ (final concentration 10 mM) to oxidize the saccharide residues of the oligosaccharides associated with the Fc portion of the antibody. Oxidation was allowed to take place for approximately 20 minutes at 0°–1° C., after which time it was terminated by addition of a sufficient volume of 100 mM glycerol to bring the final concentration of the antibody solution to 11 mM in glycerol. The reaction was allowed to quench for 20 minutes, with stirring, during which time the mixture was allowed to warm to room temperature. The reaction mixture was then diluted with two volumes of 100 mM sodium acetate/300 mM NaCl, pH 5.5, and transferred to an Amicon ultrafiltration unit fitted with a 100,000 molecular weight cutoff membrane.

The covalently-linked component-linker compound of structure V and the commercially available biotin hydrazide were each dissolved in DMSO and individually added at a 500:1 molar ratio to the antibody solution. The resultant solutions were concentrated back to their original 1 mL volume in the ultrafiltration unit. The ultrafiltration process was repeated two additional times, diluting the antibody solution each time with two volumes of buffer and a 500:1 molar excess of the covalently-linked component-linker compound or biotin hydrazide. After the third cycle, the antibody solution was concentrated to 2 mg/mL, removed from the ultrafiltration unit, and incubated overnight (500:1 molar excess). Unreacted covalently-linked component-linker compound or biotin hydrazide was removed by exchange of the resulting conjugate into storage buffer consisting of 100 mM potassium phosphate/300 mM NaCl, pH 7.4, using gel filtration chromatography.

EXAMPLE 3

STABILITY OF A REPRESENTATIVE STABLY-LINKED CONJUGATE: ACCELERATED STABILITY STUDY

The stability of the conjugates synthesized in Example 2 were evaluated under accelerated conditions by incubating each conjugate at 37° C. for 18 hours in three antibody storage buffers, the pH of which were adjusted to be 7.4, 6.4 and 5.0, respectively, using equimolar phosphoric acid or tribasic potassium phosphate. The ratio of biotin to protein (B:P) was determined using the HABA-avidin method of Green (*Biochem. J.* 94:23c, 1965). The B:P ratio for each conjugate was determined after 18 hours and compared to the B:P ratio of freshly prepared conjugate (control). The results of this experiment are summarized in Table 1 below.

TABLE 1

Conjugate B:P Ratios

| Biotin Conjugate | Biotin:IgM Ratio (B:P) | | % Bound (Control Normalized) | |
|---|---|---|---|---|
| | Semi-carbazone | Hydrazone | Semi-carbazone | Hydrazone |
| Time 0 (control) | 45 | 41 | 100 | 100 |
| pH 7.4 | 43 | 29 | 96 | 71 |
| pH 6.4 | 33 | 18 | 73 | 44 |
| pH 5.0 | 30 | 12 | 67 | 29 |

Referring to Table 1, the stability of the biotin-antibody conjugate joined by a hydrazone linkage was significantly less than that of the biotin-antibody conjugate of the present invention joined by a semicarbazone linkage. Furthermore, the biotin-antibody conjugate joined by a hydrazone linkage was pH-dependent. In contrast, the stably-linked conjugate of the present invention showed significantly less pH dependence.

EXAMPLE 4

STABILITY OF A REPRESENTATIVE STABLY-LINKED CONJUGATE LONG-TERM STABILITY

Figure 1:
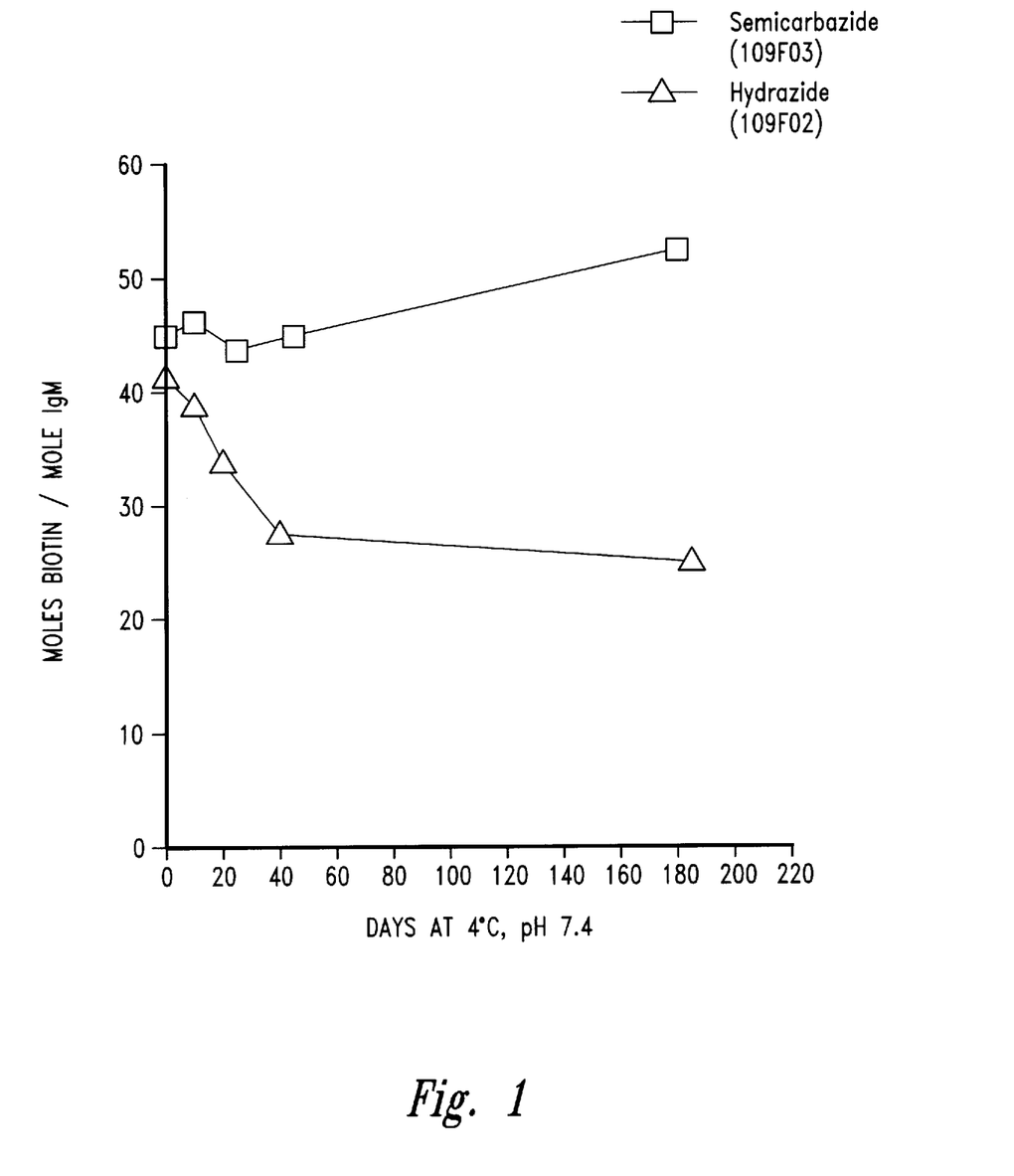
FIG. 1 illustrates storage stability of a representative stably-linked conjugate of this invention compared to a corresponding hydrazide-linked conjugate.

Biotin-antibody conjugates were prepared as disclosed in Example 2 above. The conjugates were stored at 4° C. in antibody storage buffer, pH 7.4 and their relative stability determined by withdrawing samples at various time points and assaying the B:P ratio as described above. The results of this experiment are presented in FIG. 1. Referring to FIG. 1, the biotin conjugate joined by a hydrazone linkage retained only about 65% of the biotin initially conjugated after 184 days storage. In contrast, the stably-linked conjugate of this invention retained 100% of the biotin initially conjugated after the same period of time.

EXAMPLE 5

USE OF A STABLY-LINKED CONJUGATE FOR CELL SELECTION

A stably-linked conjugate of a mouse monoclonal antibody designated 12.8 was prepared as described in Example 2 above. Antibody 12.8 binds to a determinant of the CD34 antigen, an antigen expressed on human hematopoietic stem and progenitor cells, among other cells. This antibody was conjugated to biotin hydrazide, as described in Example 2 above, and used to select CD34+ cells from human bone marrow by affinity chromatography (Berenson et al., *Advances in Bone Marrow Purging and Processing*, D. A. Worthington-White, A. P. Gee, and S. Gross, Eds., New York; Wiley-Liss, pp. 449–459, 1992).

Briefly, a buffy coat was prepared from human bone marrow by centrifugation and incubated for 25 minutes with 3 mg of stably-biotinylated antibody 12.8 (hereinafter 12.8 semicarbazone) or 12.8 conjugated to biotin via a hydrazone linkage (hereinafter 12.8 hydrazone). Following incubation, the cells were washed by centrifugation in PBS, containing 5% human serum albumin (HSA). The cells were resuspended in 150–300 mL of PBS/LISA and passed through a CEPRATE® SC column containing avidin-conjugated polyacrylamide (Biogel P30) beads (CellPro, Bothell, Wash.), according to the manufacturer's instructions. The column was washed extensively with PBS to remove unbound cells. Bound CD34+ cells were eluted from the column by mechanical agitation and collected in a volume of about 100 mL. The yield and purity of CD34 cells were determined by comparing the number of CD34+ cells pre- and post-selection, using flow cytometry according to the manufacturer's instructions.

The mean purity (n=2) of CD34+ cells using 12.8 semicarbazone was 76.2% compared to 76.6% using 12.8 hydrazone. The mean yield (n=2) of CD34+ cells using 12.8 semicarbazone was 27.3% compared to 24.4% for 12.8 hydrazone. These data indicate that the semicarbazide conjugate of 12.8 gave equivalent performance in cell selection to hydrazide conjugates of 12.8.

It will be appreciated that, although specific embodiments of the invention have been described herein for purposes of illustration, various modifications may be made without departing from the spirit and scope of the invention. Accordingly, the invention is not limited except by the appended claims.

We claim:

1. A compound having the structure:

X—(CH$_2$)$_n$—NH—C(=R$_2$)—NH—NH$_2$ wherein n=1–12; R2 is selected from O and NH; and X is selected from an animo and a protected amino group.

2. The compound of claim 1 wherein X is an amino group.
3. The compound of claim 1 wherein X is a protected amino group.
4. The compound of claim 2 or 3 wherein R$_2$ is O.
5. The compound of claim 2 or 3 wherein R$_2$ is NH.
6. The compound of claim 1 wherein n=4–6.
7. A compound having the structure:

X—(CH$_2$)$_n$—NH—C(=R$_2$)—NH—NH—P' wherein n=1–12; R$_2$ is selected from O, NH and S, X is selected from an amine and a protected amine group, and P' is a protecting group.

8. The compound of claim 7 wherein X is an amine group.

9. The compound of claim 7 wherein X is a protected amine group.

10. The compound of claim 7 or 8 wherein $R_2$ is O.

11. The compound of claim 7 or 8 wherein $R_2$ is NH.

12. The compound of claim 7 or 8 wherein $R_2$ is S.

13. The compound of claim 7 wherein X is an amino group.

14. The compound of claim 7 wherein n=4–6.

* * * * *